(12) United States Patent
Scott et al.

(10) Patent No.: US 10,071,943 B2
(45) Date of Patent: Sep. 11, 2018

(54) COPPER CATALYZED [18F]FLUORINATION OF IODONIUM SALTS

(71) Applicant: THE REGENTS OF THE UNIVERSITY OF MICHIGAN, Ann Arbor, MI (US)

(72) Inventors: Peter J. H. Scott, Ypsilanti, MI (US); Melanie S. Sanford, Ann Arbor, MI (US); Naoko Ichiishi, Ann Arbor, MI (US); Allen F. Brooks, Ann Arbor, MI (US); Melissa Rodnick, Ann Arbor, MI (US); Joseph J. Topczewski, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/303,087

(22) PCT Filed: Apr. 10, 2015

(86) PCT No.: PCT/US2015/025241
§ 371 (c)(1),
(2) Date: Oct. 10, 2016

(87) PCT Pub. No.: WO2015/157597
PCT Pub. Date: Oct. 15, 2015

(65) Prior Publication Data
US 2017/0036980 A1 Feb. 9, 2017

Related U.S. Application Data

(60) Provisional application No. 61/978,646, filed on Apr. 11, 2014.

(51) Int. Cl.
| | |
|---|---|
| *C07C 41/22* | (2006.01) |
| *A61K 51/04* | (2006.01) |
| *C07B 59/00* | (2006.01) |
| *C07C 231/12* | (2006.01) |
| *C07C 233/51* | (2006.01) |
| *C07C 67/307* | (2006.01) |
| *C07C 45/63* | (2006.01) |
| *C07C 17/361* | (2006.01) |
| *C07C 51/363* | (2006.01) |
| *C07J 1/00* | (2006.01) |

(52) U.S. Cl.
CPC ............. *C07C 41/22* (2013.01); *A61K 51/04* (2013.01); *A61K 51/0402* (2013.01); *A61K 51/0493* (2013.01); *C07B 59/00* (2013.01); *C07C 17/361* (2013.01); *C07C 45/63* (2013.01); *C07C 51/363* (2013.01); *C07C 67/307* (2013.01); *C07C 231/12* (2013.01); *C07C 233/51* (2013.01); *C07J 1/0066* (2013.01); *C07B 2200/05* (2013.01)

(58) Field of Classification Search
CPC ..... C07B 2200/05; C07B 59/00; A61K 51/04; C07C 51/363
USPC ......................................... 424/1.65
See application file for complete search history.

(56) References Cited

U.S. PATENT DOCUMENTS

| | | | |
|---|---|---|---|
| 6,087,543 A | 7/2000 | Subramanian | |
| 8,309,055 B2 | 11/2012 | Arstad et al. | |
| 8,604,213 B2 | 12/2013 | Dimagno | |
| 2012/0172208 A1 | 7/2012 | Caires et al. | |
| 2016/0317682 A1 | 11/2016 | Scott et al. | |

FOREIGN PATENT DOCUMENTS

| | | | |
|---|---|---|---|
| WO | WO-2005061415 A1 * | 7/2005 | ............. C07B 59/00 |
| WO | WO-2010/048170 A2 | 4/2010 | |
| WO | WO-2013/188554 | 12/2013 | |

OTHER PUBLICATIONS

Jager et al. J. Nucl. Med. 2008, 49: 573-586.*
Yu et al. Bioorg. Med. Chem. 17 (2009) 1982-1990.*
Merritt et al. Angew. Chem. Int. Ed. 2009, 48, 9052-9070.*
Casitas et al. JACS 2011, 133, 19386-19392.*
Soloshinka et al. Synthesis 2008, 5, 693-695.*
Kotha et al. J. Organomet. Chem. 689 (2004) 158-163.*
Tredwell et al. Angew Chem. Int. Ed 2012, 51,11426-11437.*
Phipps et al.. Science 2009, 323, 1593-1597.*
[18F]flurpiridaz and LMI 1195, Lantheus Medical, product information downloaded from the Internet at: <http://www.lantheus.com/pipeline.html> (2015).
AdreView™ lobenguane 123 Injection, GE Healthcare, Dosage Sheet (2013).
Anbarasan et al., Efficient synthesis of aryl fluorides, Angew. Chem. Int. Ed., 49:2219-222 (2010).
Brooks et al., Late-stage [$^{18}$F] fluorination: new solutions to old problems, Chem Sci., 5(12):4545-53 (2014).
Chun et al., Regiospecific syntheses of functionalized diaryliodonium tosylates via [hydroxy(tosyloxy)iodo]arenes generated in situ from (diacetoxyiodo)arenes, J. Org. Chem., 77(4):1931-8 (2012).
Fier et al., Copper-mediated fluorination of aryl iodides, J. Am. Chem. Soc., 134:10795-8 (2012).
Higuchi et al., Stable delineation of the ischemic area by the PET perfusion tracer 18F-fluorobenzyl triphenyl phosphonium after transient coronary occlusion, J. Nucl. Med., 52(6):965-9 (2011).
IASOdopa® 6-[$^{18}$F] Fluoro-L-3,4-dihydroxyphenylalanine, IASON GmbH, Product Sheet (2014).

(Continued)

Primary Examiner — Michael G Hartley
Assistant Examiner — Sean R Donohue
(74) Attorney, Agent, or Firm — Marshall, Gerstein & Borun LLP

(57) ABSTRACT

Copper-catalyzed radiofluorination of iodonium salts, iodonium salts, and compounds obtained by copper-catalyzed radiofluorination of iodonium salts are disclosed. Diagnostic and therapeutic methods involving such compounds also are disclosed.

21 Claims, No Drawings

(56) References Cited

OTHER PUBLICATIONS

Ichiishi et al., Cu-catalyzed fluorination of diaryliodonium salts with KF, Org. Lett., 15(19):5134-7 (2013).

International Preliminary Report on Patentability, International Application No. PCT/US15/25241, dated Oct. 12, 2016.

International Search Report and Written Opinion, International Application No. PCT/US15/25241, dated Jul. 14, 2015.

Kamlet et al., Application of palladium-mediated (18)F-fluorination to PET radiotracer development: overcoming hurdles to translation, PLoS One, 8(3):e59187 (2013).

Lee et al., A fluoride-derived electrophilic late-stage fluorination reagent for PET imaging, Science, 334(6056):639-42 (2011).

Lee et al., Nickel-mediated oxidative fluorination for PET with aqueous [18F] fluoride, J. Am. Chem. Soc., 134(42):17456-8 (2012).

Moore et al., A rapid microfluidic synthesis of [18F]fluoroarenes from nitroarenes, Appl. Rad. and Isotopes, 71(1):47-50 (2013).

Ross et al., Nucleophilic 18F-Fluorination of Heteroaromatic Iodonium Salts with No-Carrier-Added [18F]Fluoride, J. Am. Chem. Soc., 129(25):8018-25 (2007).

Vizamyl™ Flutemetamol F18 Injection, GE Healthcare, Dosage Sheet (2014).

Wagner et al., Three-step, "one-pot" radiosynthesis of 6-fluoro-3,4-dihydroxy-L-phenylalanine by isotopic exchange, J. Nucl. Med., 50(10):1724-9 (2009).

Ye et al., Cu(OTf)2-Mediated Fluorination of Aryltrifluoroborates with Potassium Fluoride, J. Am. Chem. Soc., 135(44):16292-5 (2013).

* cited by examiner

COPPER CATALYZED [18F]FLUORINATION OF IODONIUM SALTS

CROSS-REFERENCE TO RELATED APPLICATIONS

This application is the U.S. national phase of PCT/US2015/25241, filed Apr. 10, 2015, which claims the benefit of U.S. provisional application No. 61/978,646, filed Apr. 11, 2014, the entire respective disclosures of which are incorporated herein by reference.

GOVERNMENT RIGHTS

This invention was made with government support under grants GM073836 and EB005172 awarded by the National Institutes of Health. The government has certain rights in the invention.

BACKGROUND

Field of the Invention

The present invention generally relates to copper-catalyzed radiofluorination of iodonium salts, to iodonium salts and compounds obtained by copper-catalyzed radiofluorination of iodonium salts, and to diagnostic and therapeutic methods involving such compounds.

Brief Description of Related Technology

Positron emission tomography (PET) is a powerful and minimally invasive medical imaging technique that provides kinetic physiochemical information. The most commonly used radioisotope for PET is $^{18}F$, which offers the advantages of high resolution imaging (ca. 2.5 mm in tissue), a relatively long lifetime ($t_{1/2}$=110 min), and minimal perturbation of radioligand binding. Despite these advantages, the development of novel $^{18}F$ radiotracers is currently impeded by a paucity of general and effective radiofluorination methods. There are currently few robust synthetic procedures for the incorporation of $^{18}F$ into organic molecules with sufficient speed, selectivity, yield, radiochemical purity, and reproducibility to provide clinical imaging materials. Direct methods for the late stage nucleophilic [$^{18}F$]fluorination of electron-rich aromatic substrates remains an especially long-standing challenge in the PET community. A target of particular interest in this regard is 6-[$^{18}F$]fluoro-$_L$-DOPA (6-[$^{18}F$]fluoro-$_L$-3,4-dihydroxyphenylalanine), which serves as a valuable diagnostic for probing the regional distribution of dopamine in the human brain. While there has been much activity in the radiofluorination community aimed at accessing 6-[$^{18}F$]fluoro-$_L$-DOPA, current methods suffer from drawbacks (including low specific activity, multi-step procedures, chiral separations, and/or poor yield) that limit routine production of this material.

The majority of radiofluorination methods for electron rich aryl rings utilize electrophilic fluorinating reagents derived from [$^{18}F$]$F_2$. However, [$^{18}F$]$F_2$ production typically requires $^{19}F_2$ as a carrier gas, which leads to low specific activity (SA) radiotracers (typically <1.0 Ci/mmol) and requires specialized facilities. The development of [$^{18}F$]KF production from [$^{18}O$]water has provided the means to synthesize high SA radiotracers (>1,000 Ci/mmol) through nucleophilic substitution (typically $S_N2$ or $S_NAr$). However, the use of [$^{18}F$]KF is generally limited to the formation of primary $sp^3$-C—F bonds or $sp^2$-C—F bonds on activated electron deficient aromatics.

Two main strategies have been used to address these limitations. The first involves radiofluorination of powerful electrophiles such as diaryliodonium salts. Diaryliodonium salts bearing the 2-thienyl group have been shown to react with [$^{18}F$]KF at elevated temperatures (often ≥150° C.) to afford [$^{18}F$]fluoroarenes (Scheme 1). In these systems, the 2-thienyl group directs radiofluorination to the other aromatic ligand on iodine, with moderate to good selectivity. However, the [(thienyl)(aryl)I$^+$] starting materials are often challenging to prepare, suffer from low stability, and have a limited shelf-life. Furthermore, with electron neutral or rich substrates, these transformations frequently require high temperatures, exhibit modest regioselectivity, demonstrate limited functional group tolerance, and provide low radiochemical yields. As such, it has proven challenging to access important radiotracers, most notably 6-[$^{18}F$]fluoro-$_L$-DOPA derivatives, using this method.

Scheme 1. Uncatalyzed Radiofluorination of Thienyl Iodonium Salts

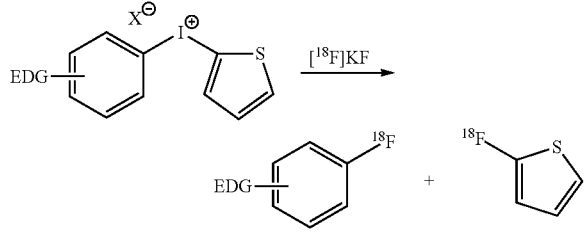

A second strategy applies transition metal catalysts and/or reagents to achieve nucleophilic radiofluorination. Transition metal catalysis offers opportunities for accelerating radiofluorination reaction rates as well as enhancing selectivity and reactivity. For instance, progress has been made in nucleophilic radiofluorination using Pd (Lee, E., *Science* 334:639 (2011); Kamlet, A. S., *PLoS One* 8:e59187 (2013)) and Ni (Lee, E., *J. Am. Chem. Soc.* 134:17456 (2012)) complexes. However, the requirement for the multistep synthesis of organometallic reagents under inert atmospheres has thus far limited adoption of these methods by non-experts.

Fluorination reactions disclosed in WO 2010/048170 also suffer from various deficiencies.

The present invention provides a general, mild, high-yielding, and user-friendly procedure for the radiofluorination of diverse aromatic substrates by merging transition metal catalysis with the fluorination of diaryliodonium salts.

SUMMARY

The present invention is directed to methods for radiofluorinating organic compounds, to compounds obtained by such methods, to diagnostic and therapeutic methods involving such compounds, and to iodonium salts useful for obtaining radiolabeled organic compounds.

In one embodiment, the present invention provides a method for radiofluorinating organic compounds by reacting a diaryliodonium salt with an $^{18}F$ source in the presence of a copper source. The diaryliodonium salt has a Formula (1):

(1)

wherein Ar¹ and Ar² independently are aryl groups; and X⁻ is an anion. The reacting is carried out under conditions sufficient to form a radiolabeled aryl fluoride of Formula (2):

(2)

In a further embodiment, the invention provides a method of diagnosing or treating a disease or condition comprising administering a radiolabeled aryl fluoride as described herein to a subject in need thereof.

Another embodiment of the present invention is a diaryliodonium salt of Formula (5)

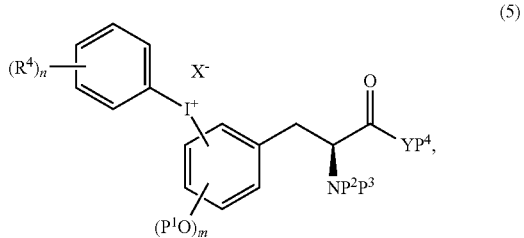
(5)

wherein X⁻ is an anion; each R⁴ is independently selected from the group consisting of methyl, ethyl, n-propyl, iso-propyl, n-butyl, sec-butyl, iso-butyl, t-butyl, aryl, and benzyl; n is selected from the group consisting of 1, 2, 3, 4, and 5; each P¹ is independently selected from alcohol protecting groups; m is selected from the group consisting of 0, 1, and 2; P² is H; and P³ is an amino protecting group; or P² and P³, taken together with the nitrogen atom to which they are attached, form a cyclic amino protecting group; Y is selected from the group consisting of O, S, and NP⁵; P⁴ is a protecting group; P⁵ is H; or P⁴ and P⁵, taken together with the nitrogen atom to which they are attached, form a cyclic amino protecting group; or P² and P⁴, taken together with the atoms to which they are attached, form a cyclic protecting group.

These and other embodiments and features of the present invention will become apparent from the following detailed description of the preferred embodiments.

DETAILED DESCRIPTION

Disclosed herein are methods for radiolabeling aryl fluorides. The methods comprise reacting a diaryliodonium salt with an ¹⁸F source in the presence of a copper source. The reacting is carried out under conditions sufficient to convert the diaryliodonium salt to an aryl fluoride to provide the radiolabeled aryl fluoride. The disclosed methods provide radiolabeled compounds having a high specific activity and utilize starting materials including electron rich, electron neutral, and electron deficient arene substrates. The disclosed methods provide various radiolabeled compounds including, but not limited to, clinically relevant compounds such as protected 4-[¹⁸F]fluoro-$_L$-phenylalanine, protected 3-[¹⁸F]fluorotyrosine, and protected 6-[¹⁸F]fluoro-$_L$-DOPA.

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

As used herein, the term "alkyl" refers to straight chained and branched hydrocarbon groups, including but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethylbutyl. The term $C_{m\text{-}n}$ means the alkyl group has "m" to "n" carbon atoms. The term "alkylene" refers to an alkyl group having a substituent. An alkyl, e.g., methyl, or alkylene, e.g., —CH₂—, group can be substituted with one or more, and typically one to three, of independently selected halo, trifluoromethyl, trifluoromethoxy, hydroxy, alkoxy, nitro, cyano, alkylamino, or amino groups, for example.

As used herein, the term "halo" refers to fluoro, chloro, bromo, and iodo.

The term "hydroxy" is defined as —OH.
The term "alkoxy" is defined as —OR, wherein R is alkyl.
The term "amino" is defined as —NH₂, and the term "alkylamino" is defined as —NR₂, wherein at least one R is alkyl and the second R is alkyl or hydrogen.
The term "carbamoyl" is defined as —C(=O)NR₂.
The term "carboxy" is defined as —C(=O)OH or a salt thereof.
The term "nitro" is defined as —NO₂.
The term "cyano" is defined as —CN.
The term "trifluoromethyl" is defined as —CF₃.
The term "trifluoromethoxy" is defined as —OCF₃.

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, alkyl, alkenyl, —OCF₃, —NO₂, —CN, —NC, —OH, alkoxy, amino, alkylamino, —CO₂H, —CO₂alkyl, —OCOalkyl, aryl, and heteroaryl.

As used herein, the term "benzyl" refers to —CH₂—phenyl. Unless otherwise indicated, a benzyl group can be unsubstituted or substituted with one or more, and in particular one to four, groups independently selected from, for example, halo, alkyl, alkenyl, —OCF₃, —NO₂, —CN, —NC, —OH, alkoxy, amino, alkylamino, —CO₂H, —CO₂alkyl, —OCOalkyl, aryl, and heteroaryl.

As used herein, the term "heterocyclic" refers to a heteroaryl and heterocycloalkyl ring systems.

As used herein, the term "heteroaryl" refers to a monocyclic or bicyclic ring system containing one or two aromatic rings and containing at least one nitrogen, oxygen, or sulfur atom in an aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl group has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, fluoropyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "cycloalkyl" means a monocyclic or bicyclic, saturated or partially unsaturated, ring system containing three to eight carbon atoms, including cyclopropyl, cyclobutyl, cyclopentyl, cyclohexyl, cycloheptyl, and cyclooctyl, optionally substituted with one or more, and typically one to three, of independently selected halo, trifluoromethyl, trifluoromethoxy, hydroxy, alkoxy, nitro, cyano, alkylamino, or amino groups, for example.

As used herein, the term "heterocycloalkyl" means a monocyclic or a bicyclic, saturated or partially unsaturated, ring system containing 4 to 12 total atoms, of which one to five of the atoms are independently selected from nitrogen, oxygen, and sulfur and the remaining atoms are carbon. Nonlimiting examples of heterocycloalkyl groups are azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, diazacycloheptyl, each optionally substituted with one or more, and typically one to three, of independently selected halo, $C_{1-6}$ alkyl, $C_{1-6}$ alkoxy, cyano, amino, carbamoyl, nitro, carboxy, $C_{2-7}$ alkenyl, $C_{2-7}$ alkynyl, or the like on an atom of the ring.

In one aspect, a method is provided for preparing a radiolabeled aryl fluoride of Formula (2) comprising reacting a diaryliodonium salt of Formula (1):

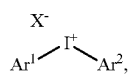
(1)

with an $^{18}$F source in the presence of a copper source under conditions sufficient to form the radiolabeled aryl fluoride of Formula (2):

(2)

wherein Ar$^1$ and Ar$^2$ independently are aryl groups; and X$^-$ is an anion.

In some embodiments, Ar$^1$ is has a structure of Formula (3):

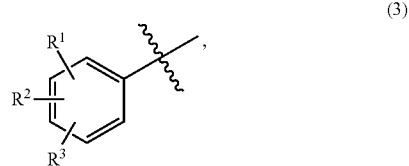
(3)

wherein R$^1$, R$^2$, and R$^3$ are independently selected from the group consisting of H, $C_{1-4}$alkyl, OR$^a$, NR$^a$R$^b$, halo, —NR$^a$C(=O)R$^b$, —C(=O)NR$^a$R$^b$, —OC(=O)R$^a$, —C(=O)OR$^a$, —C(=O)R$^a$, aryl, benzyl, and

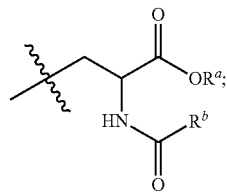

or

R$^2$ and R$^3$, taken together with the carbon atoms to which they are attached, form a 4- to 8-membered ring; R$^a$ is selected from the group consisting of H, $C_{1-4}$alkyl, aryl, and benzyl; and R$^b$ is selected from the group consisting of H, $C_{1-4}$alkyl, aryl, benzyl, —O—$C_{1-4}$alkyl, —O-aryl, and —O-benzyl; with the proviso that at least one of R$^1$, R$^2$, and R$^3$ is other than H. In some embodiments, R$^2$ and R$^3$, taken together with the carbon atoms to which they are attached, form a substituted 4- to 8-membered ring.

Ar$^1$ groups include, but are not limited to, the following:

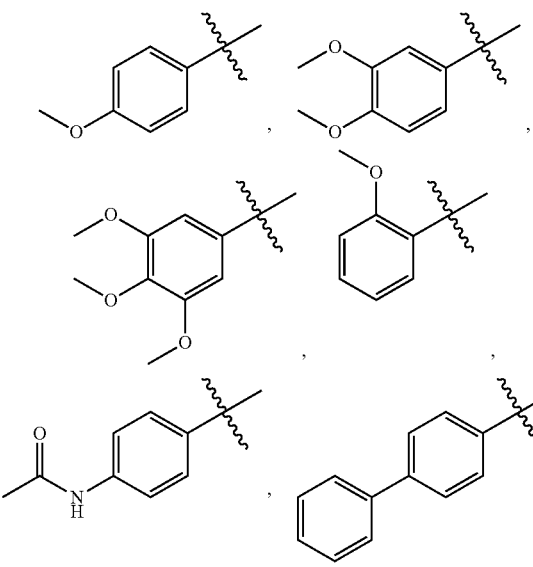

-continued

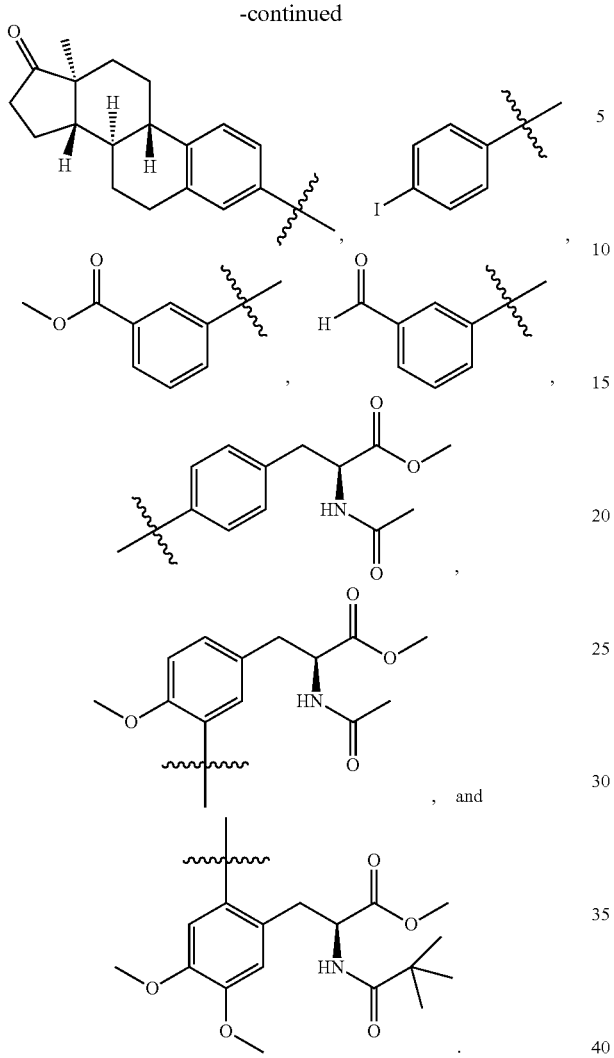

In some embodiments, Ar² has a structure of Formula (4):

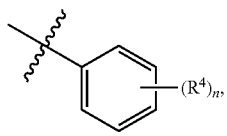
(4)

wherein each R⁴ is independently selected from the group consisting of methyl, ethyl, n-propyl, isopropyl, n-butyl, sec-butyl, iso-butyl, t-butyl, aryl, and benzyl; and n is selected from the group consisting of 1, 2, 3, 4, and 5.

In some embodiments, Ar² has the following structure:

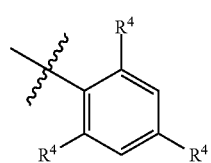

wherein each R⁴ is independently selected from the group consisting of methyl, ethyl, n-propyl, isopropyl, n-butyl, sec-butyl, iso-butyl, t-butyl, aryl, and benzyl.

Ar² groups include, but are not limited to, the following:

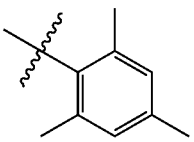

Diaryliodonium ions (i.e., ions of formula Ar¹—I⁺—Ar²) include, but are not limited to, the following:

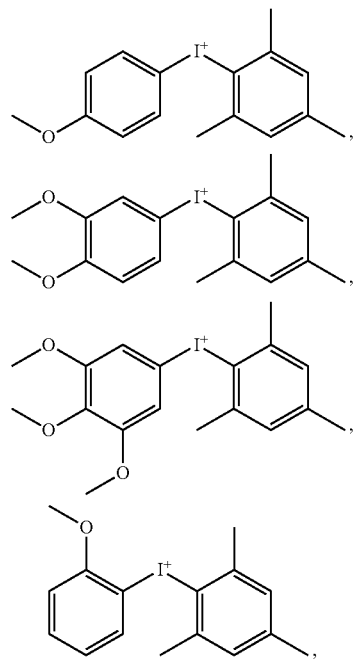

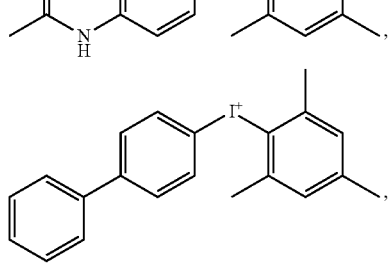

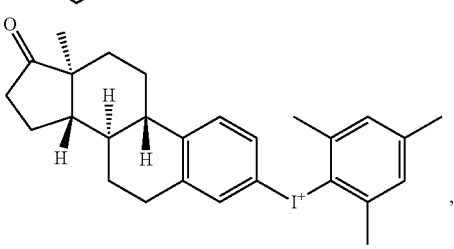

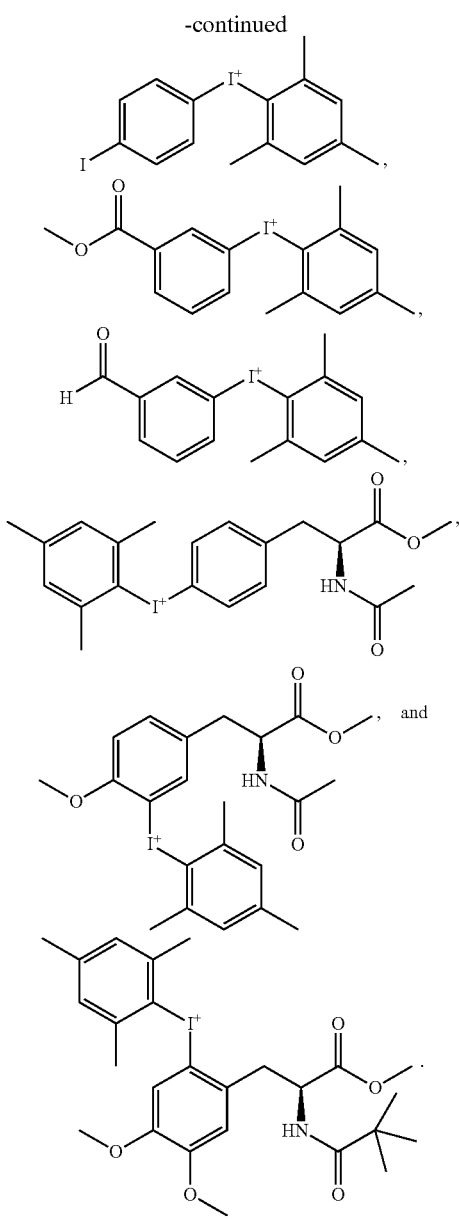

In various embodiments, the iodonium salt comprises a counteranion (i.e., X⁻) including, but not limited to, halides (e.g., fluoride, chloride, bromide, iodide), trifluoromethanesulfonate (triflate, ⁻OTf), toluene sulfonate (tosylate, ⁻OTs), tetrafluoroborate, hexafluorophosphate, methanesulfonate (mesylate), hexafluoropropanesulfonate, nonafluorobutanesulfonate (nonaflate), nitrophenyl sulfonate (nosylate), bromophenyl sulfonate (brosylate), perfluoroalkyl sulfonate (e.g., perfluoro $C_{2-10}$ alkyl sulfonate), tetraphenylborate, trifluoroacetate, perfluoroalkylcarboxylate, perchlorate, hexafluorostibate, hexachlorostibate, acetate, and benzoate.

In various embodiments, the copper source includes, but is not limited to, copper(II) trifluoromethanesulfonate (Cu(OTf)₂), copper(II) carbonate basic (CuCO₃.Cu(OH)₂), copper(I) trifluoromethanesulfonate toluene complex (CuOTf.toluene), tetrakisacetonitrile copper(I) triflate ((CH₃CN)₄CuOTf), ammonium tetrachlorocuprate(II), copper benzene-1,3,5-tricarboxylate, bis(1,3-bis(2,6-diisopropylphenyl)imidazol-2-ylidene)copper(I) tetrafluoroborate, bis[1,3-bis(2,4,6-trimethylphenyl)imidazol-2-ylidene]copper(I) tetrafluoroborate, bis(ethylenediamine)copper(II) hydroxide, (R,R)-(−)-N,N'-bis(3-hydroxylsalicylidene)-1,2-cyclohexanediaminocopper(II)samarium isopropoxide, bis [(tetrabutylammonium iodide)copper(I) iodide], [bis(trimethylsilyl)acetylene](hexafluoroacetylacetonato)copper(I), bromotris(triphenylphosphine)copper(I), 5-chlorobenzo[b] phosphindole, chloro[1,3-bis(2,6-diisopropylphenyl)imidazol-2-ylidene]copper(I), copper(I) acetate, copper(II) acetate 1,2-bis(diphenylphosphino)ethane, copper(II) acetylacetonate, copper(I) bromide, copper(I) bromide dimethyl sulfide complex, copper(II) tert-butylacetoacetate, copper(II) carbonate, copper(I) chloride, copper(II) chloride, copper(I) chloride-bis(lithium chloride) complex, copper(I) cyanide di(lithium chloride) complex, copper(II) 3,5-diisopropylsalicylate, copper (I) diphenylphosphinate, copper(II) ethylacetoacetate, copper(II) 2-ethylhexanoate, copper formate, copper hydride, copper(I) iodide, copper iodide dimethyl sulfide complex, copper(I) iodide trimethylphosphite complex, copper(I) 3-methylsalicylate, copper(II) nitrate, copper (I) oxide, copper oxychloride, copper(II) sulfate, copper(II) tartrate, copper(II) tetrafluoroborate, copper(I) thiophene-2-carboxylate, copper(I) thiophenolate, di-µ-hydroxo-bis[(N,N,N',N'-tetramethylethylenediamine)copper(II)] chloride, copper(I) trifluoromethanesulfonate benzene complex, cupric carbonate, {Cuprous 2-[(2-diphenylphosphino)benzylideneamino]-3,3-dimethylbutyrate,triflatesodium triflate} complex, (1,4-diazabicyclo[2.2.2]octane)copper(I) chloride complex, dichloro(1,10-phenanthroline)copper(II), dilithium tetrachlorocuprate(II), hydro[(4R)-[4,4'-bi-1,3-benzodioxole]-5,5'-diylbis[bis[3,5-bis(1,1-dimethylethyl)-4-methoxyphenyl]phosphine-P]]copper(I), (ethylcyclopentadienyl)(triphenylphosphine)copper(I), fluorotris (triphenylphosphine)copper(I), iodo(triethyl phosphite) copper(I), mesitylcopper(I), (1,10-phenanthroline)bis (triphenylphosphine)copper(I) nitrate dichloromethane adduct, phthalocyanine green, tetrakis(acetonitrile)copper(I) hexafluorophosphate, tetrakis(acetonitrile)copper(I) tetrafluoroborate, and tetrakis(pyridine)copper(II) triflate.

In various embodiments, the $^{18}F$ source includes, but is not limited to, $^{18}F$-labeled alkali metal fluorides and alkaline earth metal fluorides (e.g., $^{18}F$ lithium fluoride, $^{18}F$ sodium fluoride, $^{18}F$ potassium fluoride, $^{18}F$ rubidium fluoride, $^{18}F$ cesium fluoride, $^{18}F$ beryllium fluoride, $^{18}F$ magnesium fluoride, $^{18}F$ calcium fluoride), $^{18}F$-labeled ammonium fluorides (e.g., $^{18}F$-labeled tetraalkylammonium fluorides such as $^{18}F$ tetramethylammonium fluoride, $^{18}F$ tetraethylammonium fluoride, $^{18}F$ tetrapropylammonium fluoride, and $^{18}F$ tetrabutylammonium fluoride), and complexes thereof with complexing compounds such as crown ethers (e.g., complexes with 12-crown-4, 15-crown-5, 18-crown-6, dibenzo-18-crown-6, and diaza-18-crown-6), for example, $^{18}F$ potassium fluoride.18-crown-6 complex.

The $^{18}F$ fluorination reaction can be carried out in various solvents. Suitable solvents include, but are not limited to, polar protic solvents, polar aprotic solvents, nonpolar solvents, alcohols, esters, ethers, amides, glycols, glycol ethers, aliphatic and aromatic hydrocarbons, chlorinated solvents, $C_{1-6}$alcohols (e.g., methanol, ethanol, propyl alcohol, and butyl alcohol, including isomers thereof), mono$C_{1-4}$alkyl ethers of ethylene glycol and propylene glycol, acetone, methyl ethyl ketone, isophorone, dichloromethane, chloroform, ethyl acetate, 2-methoxyethanol, dimethylformamide (DMF), dimethyl sulfoxide (DMSO), tetrahydrofuran (THF), acetonitrile, kerosene, mineral spirits, xylene, toluene, and mixtures thereof.

The $^{18}$F fluorination reaction can be carried out at various molar ratios of copper source to diaryliodonium salt. Suitable molar ratios of copper source to diaryliodonium salt include, but are not limited to, about 1:20 to about 5:1, about 1:10 to about 3:1, about 1:5 to about 2:1, and/or about 1:2 to 1:1.

The $^{18}$F fluorination reaction can be carried out at various loading levels of the diaryliodonium salt. Suitable loading levels of the diaryliodonium salt include, but are not limited to, about 1 μmol or greater, about 2 μmol or greater, about 3 μmol or greater, about 4 μmol or greater, about 5 μmol or greater, about 6 μmol or greater, about 10 μmol or greater, about 20 μmol or greater, about 30 μmol or greater, about 50 μmol or greater, about 1 μmol to about 100 μmol, about 2 μmol to about 50 μmol, about 3 μmol to about 30 μmol, and/or about 5 μmol to about 20 μmol.

The $^{18}$F fluorination reaction can be carried out at various temperatures. Suitable reaction temperatures include, but are not limited to, a temperature of about 0° C. to about 150° C., such as about 20° C. to about 140° C., about 40° C. to about 130° C., about 50° C. to about 120° C., about 60° C. to about 110° C., about 70° C. to about 100° C., and/or about 80° C. to about 90° C.

The $^{18}$F fluorination reaction can be carried out for various lengths of time. Suitable reaction times include, but are not limited to, a reaction time of about 1 minute or greater, about 5 minutes or greater, about 10 minutes or greater, about 15 minutes or greater, about 20 minutes or greater, about 30 minutes or greater, and/or about 45 minutes or greater.

$^{18}$F-labeled aryl fluorides of Formula (2) prepared according to the methods disclosed herein are obtained in high radiochemical yield (RCY). For example, the products of the methods disclosed herein are obtained in a radiochemical yield of about 5% or greater, about 10% or greater, about 20% or greater, about 30% or greater, about 40% or greater, about 50% or greater, about 60% or greater, and/or about 70% or greater.

In various embodiments, the radiolabeled aryl fluoride of Formula (2) is isolated. Suitable methods of isolating the radiolabeled aryl fluoride of Formula (2) include, but are not limited to, extraction, chromatography, and crystallization.

In one aspect, the disclosure provides a method of diagnosing or treating a disease or condition comprising administering a radiolabeled aryl fluoride as described herein to a subject in need thereof. 4-[$^{18}$F]fluoro-L-phenylalanine, for example, can be used as a probe of pancreatic and cerebral protein synthesis. Advantageously, the methods described herein provide radiofluorinated compounds such as 4-[$^{18}$F]fluoro-L-phenylalanine in high specific activity and radiochemical yield.

Also provided are methods for preparing aryl fluorides comprising reacting a diaryliodonium salt with an $^{19}$F source in the presence of a copper source, wherein the reacting is carried out under conditions sufficient to convert the diaryliodonium salt to an aryl fluoride to provide the aryl fluoride. (Ichiishi, N., *Org. Lett.*, 15:5134 (2013)). Suitable diaryliodonium salts, copper sources, and conditions are described herein. Suitable $^{19}$F sources include, but are not limited to, alkali metal fluorides and alkaline earth metal fluorides (e.g., lithium fluoride, sodium fluoride, potassium fluoride, rubidium fluoride, cesium fluoride, beryllium fluoride, magnesium fluoride, calcium fluoride), ammonium fluorides (e.g., tetraalkylammonium fluorides such as tetramethylammonium fluoride, tetraethylammonium fluoride, tetrapropylammonium fluoride, and tetrabutylammonium fluoride), and complexes thereof with complexing compounds such as crown ethers (e.g., complexes with 12-crown-4, 15-crown-5, 18-crown-6, dibenzo-18-crown-6, and diaza-18-crown-6), for example, potassium fluoride.18-crown-6 complex.

In another aspect, the disclosure is directed to a compound of Formula (5):

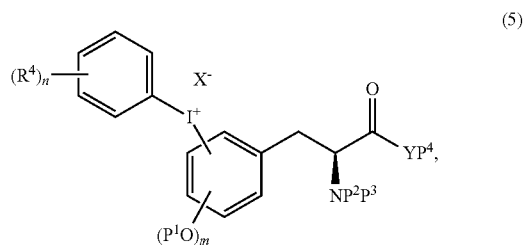

(5)

wherein $X^-$ is an anion; each $R^4$ is independently selected from the group consisting of methyl, ethyl, n-propyl, iso-propyl, n-butyl, sec-butyl, iso-butyl, t-butyl, aryl, and benzyl; n is selected from the group consisting of 1, 2, 3, 4, and 5; each $P^1$ is independently selected from alcohol protecting groups; m is selected from the group consisting of 0, 1, and 2; $P^2$ is H; $P^3$ is an amino protecting group; or $P^2$ and $P^3$, taken together with the nitrogen atom to which they are attached, form a cyclic amino protecting group; Y is selected from the group consisting of O, S, and $NP^5$; $P^4$ is a protecting group; $P^5$ is H; or $P^4$ and $P^5$, taken together with the nitrogen atom to which they are attached, form a cyclic amino protecting group; or $P^2$ and $P^4$, taken together with the atoms to which they are attached, form a cyclic protecting group. Suitable anions include, but are not limited to, fluoride, chloride, bromide, iodide, trifluoromethanesulfonate, toluene sulfonate, tetrafluoroborate, hexafluorophosphate, methanesulfonate, hexafluoropropanesulfonate, nonafluorobutanesulfonate, nitrophenyl sulfonate, bromophenyl sulfonate, perfluoroalkyl sulfonate, tetraphenylborate, trifluoroacetate, perfluoroalkylcarboxylate, perchlorate, hexafluorostibate, hexachlorostibate, acetate, and benzoate.

In some embodiments, the compound of Formula (5) has a structure of Formula (6)

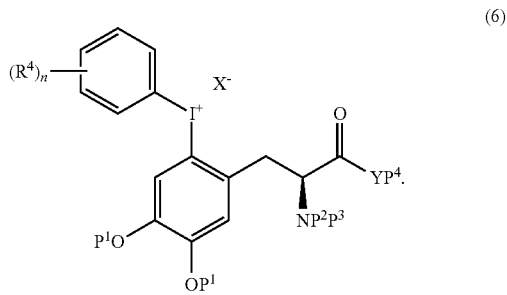

(6)

In some embodiments, the compound of Formula (5) has a structure of Formula (7)

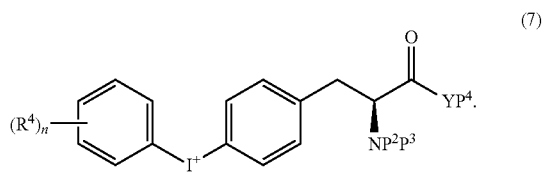

(7)

In some embodiments, the compound of Formula (5) has a structure of Formula (8)

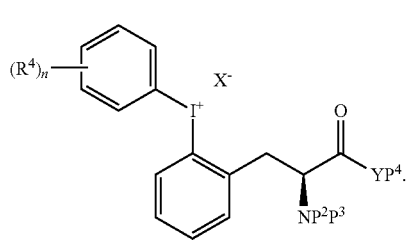

(8)

In some embodiments, the compound of Formula (5) has a structure of (9)

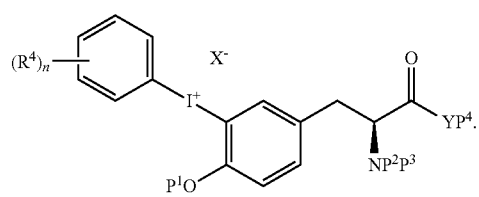

(9)

Various protecting groups can be used. Suitable protecting groups include, but are not limited to, protecting groups of formula $R^a$, —C(=O)$R^a$, and —C(=O)O$R^a$, wherein $R^a$ is $C_{1-4}$alkyl, aryl, and benzyl. For example, suitable protecting groups include methyl, acetyl, and pivaloyl. In some embodiments, $P^1$, $P^3$, and $P^4$ are independently selected from the group consisting of $R^a$, —C(=O)$R^a$, and —C(=O)O$R^a$; wherein $R^a$ is selected from the group consisting of $C_{1-4}$alkyl, aryl, and benzyl.

In some embodiments, $P^2$ and $P^3$, taken together with the nitrogen atom to which they are attached, form a cyclic amino protecting group having the structure:

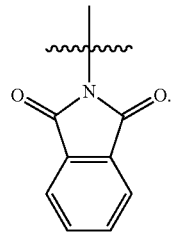 [SMILES: *N1C(=O)c2ccccc2C1=O]

In some embodiments, $P^2$ and $P^4$, taken together with the atoms to which they are attached, form a cyclic protecting group having the structure:

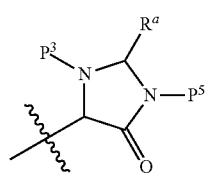

wherein $R^a$ is selected from the group consisting of H, $C_{1-4}$alkyl, aryl, and benzyl. For example, $P^2$ and $P^4$, taken together with the atoms to which they are attached, form a cyclic protecting group having the structure:

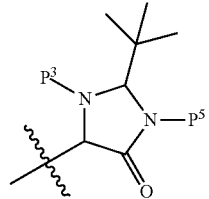

and/or the structure:

EXAMPLES

Example 1—Synthesis of [$^{18}$F]KF.18-Crown-6 Complex

Potassium [$^{18}$F]fluoride was prepared using a TRACER-Lab FXFN automated radiochemistry synthesis module (General Electric, GE). All loading operations were conducted under ambient atmosphere. Argon was used as a pressurizing gas during automated sample transfers. [$^{18}$F] Fluoride was produced via the $^{18}$O(p,n)$^{18}$F nuclear reaction using a GE PETTrace cyclotron (40 μA beam for 2 min generated ca. 150 mCi of [$^{18}$F]fluoride). The [$^{18}$F]fluoride was delivered to the synthesis module in a 1.5 mL bolus of [$^{18}$O]water and trapped on a QMA-light Sep-Pak to remove [$^{18}$O]water. [$^{18}$F]Fluoride was eluted into the reaction vessel using aqueous potassium carbonate (3.5 mg in 0.5 mL of water). A solution of 18-crown-6 (15 mg in 1 mL of acetonitrile) was added to the reaction vessel, and the resulting solution was dried by azeotropic distillation to give dry [$^{18}$F]KF.18-crown-6. Evaporation was achieved by heating the reaction vessel to 100° C. and drawing vacuum for 4 min. After this time, the reaction vessel was subjected to an argon stream and simultaneous vacuum draw for an additional 4 min. Finally, N,N-dimethylformamide (8 mL) was added to the dried reagent, and the resulting solution was transferred to a sterile vial for subsequent use in reactions (approx. 30 mCi of prepared $^{18}$F reagent was transferred).

Example 2—General Procedure for Manual Synthesis of $^{18}$F-Labeled Compounds On the bench top, solid [Mes-I—Ar]X (6 μmol) was weighed into a 4 mL amber glass vial containing a stir bar and was then dissolved in DMF (350 μL). A stock solution of tetrakis(acetonitrile)copper(I) triflate (CuOTf) was prepared (14.3 mg in 1 mL of anhydrous DMF, 0.04 M), and aliquots of this solution were used for several reactions. A 150 µL aliquot of CuOTf solution (6 µmol) was added to the vial containing [Mes-I—Ar]X. The reaction vial was sealed under an atmosphere of ambient air with a PTFE/Silicone septum cap, and then the solution was thoroughly mixed (vortex shaker, Barnstead® Thermolyne Type 16700). Via a syringe, a 250 µL aliquot of [$^{18}$F]KF·18-crown-6 complex (typically 300-700 µCi, prepared as described in Example 1) was added to the reaction vial. The vial was then heated in an aluminum block with stirring at 85° C. for 20 min. After 20 min, the reaction was allowed to cool to room temperature. A 100 µL aliquot was withdrawn from the vial and added to 400 or 900 µL of $CH_2Cl_2$ in a 4 mL vial (choice of volume of $CH_2Cl_2$ was dependent on activity). The $CH_2Cl_2$ mixture was shaken by hand and then used for radio-TLC analysis to obtain radiochemical yields (RCY). In addition, a 100 µL aliquot of the reaction solution was used for radio-HPLC analysis by diluting the sample into 50/50 MeCN/$H_2O$ (300 µL total volume).

Example 3—General Procedure for Automated Synthesis of $^{18}$F-Labeled Compounds The production-scale synthesis of radiolabeled arenes was conducted using a TRACERLab FXFN automated radiochemistry synthesis module (General Electric, GE). The synthesis module was pre-charged with a solution of the [Mes-I—Ar]X precursor (18 µmol) and tetrakisacetonitrile copper(I) triflate (8.0 mg, 20 µmol) in DMF (0.75 mL) to be added from an automated port prior to $^{18}$F delivery. [$^{18}$F] Fluoride was produced via the $^{18}$O(p,n)$^{18}$F nuclear reaction using a GE PETTrace cyclotron (40 µA beam for 30 min generated 1,500 mCi of [$^{18}$F]fluoride). The [$^{18}$F]fluoride was delivered to the synthesis module (in a 1.5 mL bolus of [$^{18}$O]water) and trapped on a QMA-light Sep-Pak to remove [$^{18}$O]water. [$^{18}$F]Fluoride was eluted into the reaction vessel using aqueous potassium carbonate (3.0 mg in 0.5 mL of water). A solution of 18-crown-6 (5 mg in 1 mL of acetonitrile) was added to the reaction vessel, and the resulting solution was dried by azeotropic distillation to give dry [$^{18}$F]KF·18-crown-6. Evaporation was achieved by heating the reaction vessel to 100° C. and drawing vacuum for 4 min. After this time, the reaction vessel was subjected to an argon stream and simultaneous vacuum draw for an additional 4 min. The reaction vessel was cooled to 50° C., DMF (0.75 mL) was added, and the resulting mixture was stirred for 1 min. A preloaded solution of iodonium salt and copper was added to the reaction vessel, and the vessel was sealed, heated to 85° C., and held at that temperature for 20 min. The reaction vessel was then cooled to 50° C., and DMF (8.5 mL) was added. The additional DMF was used to reduce hand exposure during sample manipulations and analysis. The resulting solution (10 mL) was transferred to a sterile vial for analysis (radio-TLC and radio-HPLC).

Example 4—Manual Synthesis of 4-[$^{18}$F]Fluoroanisole

4-[$^{18}$F]Fluoroanisole was prepared by the general procedure for manual synthesis of $^{18}$F-labeled compounds described in Example 2, except that the copper catalyst, diaryliodonium salt, and reaction conditions were as shown in Table 1.

TABLE 1

Synthesis of 4-[$^{18}$F]Fluoroanisole

| Example | [Cu] | X | RCY* of 4-[$^{18}$F]Fluoranisole |
|---|---|---|---|
| 4a[†] | Cu(OTF)$_2$ | BF$_4$ | 36 ± 19% (n = 15) |
| 4b[†] | CuCO$_3$·Cu(OH)$_2$ | BF$_4$ | 10 ± 6% (n = 3) |
| 4c[†] | CuOTf·toluene | BF$_4$ | 43 ± 15% (n = 3) |
| 4d[†] | (CH$_3$CN)$_4$CuOTf | BF$_4$ | 70 ± 11% (n = 11) |
| 4e[†] | none | BF$_4$ | <1% |
| 4f[‡] | (CH$_3$CN)$_4$CuOTf | BF$_4$ | 79 ± 8% (n = 38) |
| 4g[‡] | (CH$_3$CN)$_4$CuOTf | PF$_6$ | 53 ± 7% (n = 3) |
| 4h[‡] | (CH$_3$CN)$_4$CuOTf | OTs | 45 ± 26% (n = 3) |
| 4i[‡] | (CH$_3$CN)$_4$CuOTf | OTf | <1% |
| 4j[‡] | (CH$_3$CN)$_4$CuOTf | Br | <1% |

*Radiochemical Yield (RCY) was determined by radio-TLC (average of n runs). The identity of 4-[$^{18}$F]fluoroanisole was confirmed by HPLC.
[†]Conditions: [4-OMePh-I-Mes]X (6 µmol), [Cu] (3 µmol), [$^{18}$F]KF·18-crown-6 in DMF (250 µL, 300-700 µCi), total volume 750 µL.
[‡]Conditions: [4-OMePh-I-Mes]X (6 µmol), [Cu] (6 µmol), [$^{18}$F]KF·18-crown-6 in DMF (250 µL, 300-700 µCi), total volume 750 µL.

As demonstrated in Table 1, 6 µmol [4-OMePh-I-Mes]BF$_4$ was converted to 4-[$^{18}$F]fluoroanisole in 36% radiochemical yield (RCY) in 20 min at 85° C. with 3 µmol Cu(OTf)$_2$ as the catalyst (1:2 ratio of copper catalyst to diaryliodonium salt), DMF as the solvent, and [$^{18}$F]KF-18-crown-6 as the fluoride source (Example 4a). High selectivity was observed for 4-[$^{18}$F]fluoroanisole, with <1% of [$^{18}$F]fluoromesitylene detected by radio-TLC or radio-HPLC. The reaction demonstrated reproducibility of ±19% yield over 15 runs.

Also as demonstrated in Table 1, 6 µmol [4-OMePh-I-Mes]BF$_4$ was converted to 4-[$^{18}$F]fluoroanisole in 70% radiochemical yield (RCY) in 20 min at 85° C. with 3 µmol (CH$_3$CN)$_4$CuOTf as the catalyst (1:2 ratio of copper catalyst to diaryliodonium salt), DMF as the solvent, and [$^{18}$F]KF-18-crown-6 as the fluoride source (Example 4d). The reaction demonstrated reproducibility of ±11% yield over 11 runs. Additionally as demonstrated in Table 1, 6 µmol [4-OMePh-I-Mes]BF$_4$ was converted to 4-[$^{18}$F]fluoroanisole in 79% radiochemical yield (RCY) in 20 min at 85° C. with 6 µmol (CH$_3$CN)$_4$CuOTf as the catalyst (1:1 ratio of copper catalyst to diaryliodonium salt), DMF as the solvent, and [$^{18}$F]KF-18-crown-6 as the fluoride source (Example 4f). The reaction demonstrated reproducibility of ±8% yield over 38 runs.

Example 4e demonstrated that in the absence of copper catalyst, no detectable 4-[$^{18}$F]fluoroanisole was obtained and only 6% RCY [$^{18}$F]fluoromesitylene was obtained.

Example 5—Manual Synthesis of 4-[$^{18}$F]Fluoroanisole

4-[$^{18}$F]Fluoroanisole was prepared by the general procedure for manual synthesis of $^{18}$F-labeled compounds described in Example 2, except that the molar ratio of copper catalyst and diaryliodonium salt were as shown in Table 2.

TABLE 2

Molar Ratio of $(CH_3CN)_4CuOTf$ to $[4\text{-OMePh-I-Mes}]BF_4$ $[4\text{-OMePh-I-Mes}]BF_4 \xrightarrow[\text{DMF, 85 °C, 20 min}]{(CH_3CN)_4CuOTf,\ K^{18}F\cdot 18\text{-crown-6}} 4\text{-}[^{18}F]\text{fluoroanisole}$

| Example* | [Cu]:Ar$_2$I$^+$ | % RCY |
|---|---|---|
| 5a | 0:1 | <1% (n = 11) |
| 5b | 1:5 | 55 ± 5% (n = 3) |
| 5c | 1:2 | 70 ± 11% (n = 11) |
| 5d | 1:1 | 79 ± 8% (n = 28) |
| 5e | 2:1 | 45 ± 9% (n = 3) |

*Conditions: [4-OMePh-I-Mes]BF$_4$ (6 μmol, (CH$_3$CN)$_4$CuOTf (varies), [$^{18}$F]KF•18-crown-6 in DMF (250 μL, 300-700 μCi), total volume 750 μL.

As demonstrated in Table 2, 6 μmol [4-OMePh-I-Mes]BF$_4$ was converted to 4-[$^{18}$F]fluoroanisole in 79% radiochemical yield (RCY) in 20 min at 85° C. with 6 μmol (CH$_3$CN)$_4$CuOTf as the catalyst (1:1 ratio of copper catalyst to diaryliodonium salt), DMF as the solvent, and [$^{18}$F]KF-18-crown-6 as the fluoride source (Example 5d). The reaction demonstrated reproducibility of ±8% yield over 28 runs.

Example 6—Manual Synthesis of 4-[$^{18}$F]Fluoroanisole

4-[$^{18}$F]Fluoroanisole was prepared by the general procedure for manual synthesis of $^{18}$F-labeled compounds described in Example 2, except that the loading of copper catalyst and diaryliodonium salt were as shown in Table 3.

TABLE 3

Loading of [4-OMePh-I-Mes]BF$_4$ and (CH$_3$CN)$_4$CuOTf

| Example* | μmol [4-OMePh-I-Mes]BF$_4$ and (CH$_3$CN)$_4$CuOTf | % RCY |
|---|---|---|
| 6a | 6 | 79 ± 8% (n = 37) |
| 6b | 3 | 68 ± 4% (n = 3) |
| 6c | 11 | 72 ± 3% (n = 3) |
| 6d | 23 | 48 ± 11% (n = 3) |

*Conditions: [4-OMePh-I-Mes]BF$_4$ (3-23 μmol), (CH$_3$CN)$_4$CuOTf (3-23 μmol, [$^{18}$F]KF•18-crown-6 in DMF (250 μL, 300-700 μCi), total volume 750 μL.

As demonstrated in Table 3, 6 μmol [4-OMePh-I-Mes]BF$_4$ was converted to 4-[$^{18}$F]fluoroanisole in 79% radiochemical yield (RCY) in 20 min at 85° C. with 6 μmol (CH$_3$CN)$_4$CuOTf as the catalyst (1:1 ratio of copper catalyst to diaryliodonium salt), DMF as the solvent, and [$^{18}$F]KF-18-crown-6 as the fluoride source (Example 6a). The reaction demonstrated reproducibility of ±8% yield over 37 runs.

Example 7—Manual Synthesis of 4-[$^{18}$F]Fluoroanisole

4-[$^{18}$F]Fluoroanisole was prepared by the general procedure for manual synthesis of $^{18}$F-labeled compounds described in Example 2, except that the temperature was as shown in Table 4.

TABLE 4

Reaction Temperature

| Example* | Temperature (° C.) | % RCY (n = 3) |
|---|---|---|
| 7a | 60 | 39 ± 8% |
| 7b | 85 | 76 ± 3% |
| 7c | 100 | 43 ± 16% |
| 7d | 115 | 52 ± 12% |

*Conditions: [4-OMePh-I-Mes]BF$_4$ (6 μmol, (CH$_3$CN)$_4$CuOTf (6 μmol, [$^{18}$F]KF•18-crown-6 in DMF (250 μL, 300-700 μCi), total volume 750 μL.

As demonstrated in Table 4, 6 μmol [4-OMePh-I-Mes]BF$_4$ was converted to 4-[$^{18}$F]fluoroanisole in 76% radiochemical yield (RCY) in 20 min at 85° C. with 6 μmol (CH$_3$CN)$_4$CuOTf as the catalyst (1:1 ratio of copper catalyst to diaryliodonium salt), DMF as the solvent, and [$^{18}$F]KF-18-crown-6 as the fluoride source (Example 7b). The reaction demonstrated reproducibility of ±3% yield over 3 runs. As temperature was increased, additional peaks were observed in the UV trace of the HPLC analysis.

Example 8—Manual Synthesis of 4-[$^{18}$F]Fluoroanisole

4-[$^{18}$F]Fluoroanisole was prepared by the general procedure for manual synthesis of $^{18}$F-labeled compounds described in Example 2, except that the reaction time was as shown in Table 5.

TABLE 5

Reaction Time

[Scheme: 4-OMePh-I-Mes BF₄⁻ salt + (MeCN)₄CuOTf, K¹⁸F·18-crown-6, DMF, 85 °C, Time → 4-[¹⁸F]fluoroanisole]

| Example* | Time (min) | % RCY (n = 2) |
|---|---|---|
| 8a | 5 | 33 ± 2% |
| 8b | 10 | 55 ± 10% |
| 8c | 15 | 52 ± 35% |
| 8d | 20 | 69 ± 1% |
| 8e | 30 | 65 ± 5% |
| 8f | 45 | 64 ± 8% |

*Conditions: [4-OMePh-I-Mes]BF₄ (6 μmol), (CH₃CN)₄CuOTf (6 μmol), [¹⁸F]KF·18-crown-6 in DMF (250 μL, 300-700 μCi), total volume 750 μL.

As demonstrated in Table 5, 6 μmol [4-OMePh-I-Mes]BF₄ was converted to 4-[¹⁸F]fluoroanisole in 69% radiochemical yield (RCY) in 20 min at 85° C. with 6 μmol (CH₃CN)₄CuOTf as the catalyst (1:1 ratio of copper catalyst to diaryliodonium salt), DMF as the solvent, and [¹⁸F]KF-18-crown-6 as the fluoride source (Example 8d). The reaction demonstrated reproducibility of ±1% yield over 2 runs.

Example 9—Automated Synthesis of 4-[¹⁸F]Fluoroanisole

4-[¹⁸F]Fluoroanisole was prepared by the general procedure for automated synthesis of ¹⁸F-labeled compounds described in Example 3 with 1500 mCi initial activity of ¹⁸F. Under automated conditions, [4-OMePh-I-Mes]BF₄ was converted to 4-[¹⁸F]fluoroanisole in a radiochemical yield (RCY) of 40±10% and a specific activity (SA) of 1800±800 Ci/mmol (n=3). Additionally, [4-OMePh-I-Mes]OTs was converted to 4-[¹⁸F]fluoroanisole in a radiochemical yield (RCY) of 10±2% with a SA of 3000±1000 Ci/mmol (n=3). These results indicated that isotopic dilution via ¹⁸F/¹⁹F exchange between the [¹⁹F]BF₄⁻ counterion and the [¹⁸F]KF is not significant under these reaction conditions.

Example 10—[¹⁸F]Fluorination of Mesityl Aryliodonium Salts

Mesityl aryliodonium salts were converted to [¹⁸F]-labeled compounds by the general procedure for manual synthesis of ¹⁸F-labeled compounds described in Example 2, except that the copper catalyst, diaryliodonium salt, and reaction conditions were as shown in Table 6.

TABLE 6

[¹⁸F]Fluorination of Mesityl Aryliodonium Salts

[Scheme: R-Ar-I⁺-Mes BF₄⁻ + (CH₃CN)₄CuOTf, [¹⁸F]KF·18-crown-6, DMF, 85 °C, 20 min → R-Ar-¹⁸F]

| Example | Mesityl Aryliodonium Precursor | Product | RCY* |
|---|---|---|---|
| 10a† | 4-MeO-C₆H₄-I⁺-Mes | 4-[¹⁸F]fluoroanisole | 79 ± 8% (n = 38) |
| 10b† | 3,4-(MeO)₂-C₆H₃-I⁺-Mes | 3,4-(MeO)₂-C₆H₃-¹⁸F | 51 ± 6% (n = 5) |
| 10c† | 3,4,5-(MeO)₃-C₆H₂-I⁺-Mes | 3,4,5-(MeO)₃-C₆H₂-¹⁸F | 14 ± 1% (n = 5) |

TABLE 6-continued

[¹⁸F]Fluorination of Mesityl Aryliodonium Salts

| Example | Mesityl Aryliodonium Precursor | Product | RCY* |
|---|---|---|---|
| 10d[†] | | | 30 ± 8% (n = 6) |
| 10e[†] | | | 66 ± 2% (n = 3) |
| 10f[†] | | | 51 ± 8% (n = 3) |
| 10g[†] | | | 67 ± 2% (n = 3) |
| 10h[†] | | | 35 ± 8% (n = 3) |
| 10i[†] | | | 58 ± 4% (n = 3) |
| 10j[†] | | | 35 ± 1% (n = 3) |

*Radiochemical Yield (RCY) was determined by radio-TLC (average of n runs). The identity of each product was confirmed by HPLC.
[†]Conditions: Precursor (6 μmol), [Cu] (6 μmol), [¹⁸F]KF•18-crown-6 in DMF (250 μL, 300-700 μCi), total volume 750 μL.

All of the reactions in Table 6 were highly selective for a single $^{18}$F-containing product, with ≤2% fluoromesitylene detected. Additionally, for each of the substrates, ≤2% of the corresponding fluoroarene product was observed in the absence of Cu catalyst.

As demonstrated in Table 1, arenes containing multiple electron-donating methoxy substituents were converted to the corresponding [$^{18}$F]fluorinated compound (Examples 10b and 10c). Also as demonstrated in Table 1, electron neutral and electron deficient aryl rings were converted to the corresponding [$^{18}$F]fluorinated compound (Examples 10f, 10g, 10h, 10i, and 10j). Additionally as demonstrated in Table 1, aryl rings having a variety of functional groups including amides, ketones, iodides, esters, and aldehydes were converted to the corresponding [$^{18}$F]fluorinated compound (Examples 10e, 10g, 10h, 10i, and 10j).

Example 11—Synthesis of (Mesityl)(N-(Tert-Butylcarbonyl)-3,4-Di(Methoxy)-L-Phenylalanine Methyl Ester)-2-Iodonium Tosylate (Mesityl)(N-(tert-butylcarbonyl)-3,4-di(methoxy)-L-phenylalanine methyl ester)-2-iodonium tosylate was prepared by the following 6 step synthesis.

Steps 1 and 2. Synthesis of N-(tert-butylcarbonyl)-3,4-di(tertbutylcarbonyl)-L-phenylalanine methyl ester. To an ice cold solution of L-DOPA (3.34 g, 17 mmol, 1.0 equiv Acros) in MeOH (50 mL), SOCl$_2$ (1.5 mL, 21 mmol, 1.2 equiv) was added dropwise. The solution was slowly warmed to 50° C. After 22 h, the reaction mixture was concentrated under vacuum. To remove volatile byproducts, the mixture was re-dissolved in MeOH and re-concentrated. EtOAc (25 mL) was then added, and the solution was re-concentrated under vacuum to remove residual MeOH. The crude DOPA-NH$_3$Cl—OMe was used in the next step without further purification.

An aliquot of the oil prepared above (1.3 g, assume 5.2 mmol) was dissolved in pyridine (10 mL, 124 mmol) at room temperature. Pivaloyl chloride (4 mL, 32 mmol) was added dropwise. After 20 h at room temperature, the solution was poured onto 2M HCl. The resulting solution was extracted with EtOAc (3×20 mL). The combined organic layers were washed with water, washed with brine, dried over Na$_2$SO$_4$, filtered, and concentrated under vacuum. Final purification via flash chromatography (100 g Biotage® SNAP silica column, gradient from 0% to 100% EtOAc in hexanes, R$_f$=0.4 in 30% EtOAc in hexanes) afforded N-(tert-butylcarbonyl)-3,4-di(tertbutylcarbonyl)-L-phenylalanine methyl ester as an oil (2.2 g, 15.3 mmol, 90% yield over two steps).

Step 3. N-(tert-butylcarbonyl)-2-iodo-3,4-di(tertbutylcarbonyl)-L-phenylalanine methyl ester was prepared by the following procedure adapted from the literature (Lee, E., J. Am. Chem. Soc., 134:17456 (2012)). A solution of N-(tert-butylcarbonyl)-3,4-di(tertbutylcarbonyl)-L-phenylalanine methyl ester (2.20 g, 4.8 mmol, 1.0 equiv) in CH$_2$Cl$_2$ (50 mL) was cooled in an ice bath. To this solution, solid molecular iodine (1.51 g, 6.4 mmol, 1.3 equiv) was added followed by solid [bis(trifluoroacetoxy)iodo]benzene (2.5 g, 5.8 mmol, 1.2 equiv). The solution was allowed to slowly warm to room temperature. After 24 h, the reaction was quenched by the addition of an aqueous solution of Na$_2$S$_2$O$_3$, and the deep red color of iodine rapidly faded. The resulting solution was extracted with CH$_2$Cl$_2$ (3×20 mL). The combined organic layers were dried over Na$_2$SO$_4$, filtered, and concentrated under vacuum. Final purification via flash chromatography (100 g Biotage® SNAP silica column, gradient from 0% to 100% EtOAc in hexanes, R$_f$=0.5 in 30% EtOAc in hexanes) afforded N-(tert-butylcarbonyl)-2-iodo-3,4-di(tertbutylcarbonyl)-L-phenylalanine methyl ester as an oil (337 mg, 3.9 mmol, 81% yield).

Step 4. Synthesis of N-(tert-butylcarbonyl)-2-iodo-3,4-di(methoxy)-L-phenylalanine methyl ester. A flask was charged with N-(tert-butylcarbonyl)-2-iodo-3,4-di(tertbutylcarbonyl)-L-phenylalanine methyl ester (545 mg, 0.92 mmol, 1.0 equiv), and it was brought inside of a glove box. Sodium methoxide (113 mg, 2.1 mmol, 2.3 equiv) was added as a solid. The solids were then dissolved in DMF (6 mL) at room temperature, and the flask was sealed and removed from the glove box. After 2 h, methyl iodide (0.2 mL, 3.2 mmol, 3.5 equiv) was added via syringe. After an additional 2 h at room temperature, the reaction was quenched by the addition of water. The resulting solution was extracted with EtOAc (3×20 mL). The combined organic layers were dried over Na$_2$SO$_4$, filtered, and concentrated under vacuum. Final purification via flash chromatography (25 g Biotage® SNAP silica column, gradient from 0% to 100% EtOAc in hexanes, R$_f$=0.5 in 30% EtOAc in hexanes) afforded N-(tert-butylcarbonyl)-2-iodo-3,4-di(methoxy)-L-phenylalanine methyl ester as an oil (337 mg, 0.75 mmol, 81% yield).

Step 5. Synthesis of N-(tert-butylcarbonyl)-2-trimethylstannyl-3,4-di(methoxy)-L-phenylalanine methyl ester. A 20 mL vial was charged with N-(tert-butylcarbonyl)-2-iodo-3,4-di(methoxy)-L-phenylalanine methyl ester (335 mg, 0.75 mmol, 1.0 equiv), and it was brought inside of a glove box. Lithium chloride (151 mg, 3.6 mmol, 4.8 equiv) and Pd(PPh$_3$)$_4$ (172 mg, 0.15 mmol, 0.2 equiv) were added as solids. The combined solids were then dissolved in PhMe (10 mL) at room temperature. Hexamethylditin (0.8 mL, 3.9 mmol, 5.2 equiv) was added via syringe, and the vial was sealed and removed from the glove box. The sealed vial was heated to 100° C. The initially yellow solution turned black during the course of the reaction. After 2 h, the vial was cooled to room temperature, and the solution was filtered through celite and concentrated under vacuum. Final purification via flash chromatography (25 g Biotage® SNAP silica column, gradient from 0% to 100% EtOAc in hexanes, R$_f$=0.5 in 30% EtOAc in hexanes) afforded N-(tert-butylcarbonyl)-2-trimethylstannyl-3,4-di(methoxy)-L-phenylalanine methyl ester as a light yellow oil (249 mg, 0.51 mmol, 68% yield).

Step 6. Synthesis of (mesityl)(N-(tert-butylcarbonyl)-3,4-di(methoxy)-L-phenylalanine methyl ester)-2-iodonium tosylate was accomplished by following a procedure adapted from the literature (Chun, J. H., J. Org. Chem., 77:1931 (2012)). A 20 mL vial was charged with a solution of N-(tert-butylcarbonyl)-2-trimethylstannyl-3,4-di(methoxy)-L-phenylalanine methyl ester (247 mg, 0.51 mmol, 1.0 equiv) in CH$_2$Cl$_2$ (10 mL). Solid MesI(OH)(OTs) (254 mg, 0.59 mmol, 1.2 equiv) was added at room temperature. After 50 min, the solution was concentrated under a stream of nitrogen. Final purification via flash chromatography (25 g Biotage® SNAP silica column, gradient from 0% to 100% iPrOH in CH$_2$Cl$_2$, R$_f$=0.5 in 10% iPrOH in CH$_2$Cl$_2$) afforded (mesityl)(N-(tert-butylcarbonyl)-3,4-di(methoxy)-L-phenylalanine methyl ester)-2-iodonium tosylate as a colorless oil (233 mg, 0.32 mmol, 62% yield). The oil could be solidified by dissolving it in CH$_2$Cl$_2$ followed by the slow addition of hexanes. The mixture of solvents was then removed under vacuum to afford a white solid.

Example 12—Synthesis of Protected 4-[$^{18}$F]Fluoro-$_L$-Phenylalanine, Protected 3-[$^{18}$F]Fluorotyrosine, and Protected 6-[$^{18}$F]Fluoro-$_L$-DOPA Protected 4-[$^{18}$F]fluoro-$_L$-phenylalanine, protected 3-[$^{18}$F]fluorotyrosine, and protected 6-[$^{18}$F]fluoro-$_L$-DOPA were prepared by the general procedure for manual synthesis of $^{18}$F-labeled compounds described in Example 2, except that the copper catalyst, diaryliodonium salt, and reaction conditions were as shown in Table 7.

TABLE 7

Synthesis of Protected 4-[$^{18}$F]Fluoro-$_L$-Phenylalanine, Protected 3-[$^{18}$F]Fluorotyrosine, and Protected 6-[$^{18}$F]Fluoro-$_L$-DOPA

| Example | Mesityl Aryliodonium Salt | Product | RCY* |
|---|---|---|---|
| 12a† | (structure with mesityl-I⁺-aryl, BF$_4^-$, phenylalanine methyl ester N-acetyl) | (4-[$^{18}$F]fluoro phenylalanine methyl ester N-acetyl) | 23 ± 6% (n = 3) |
| 12b† | (structure with methoxy aryl-I⁺-mesityl, TsO⁻, tyrosine methyl ester N-acetyl) | (3-[$^{18}$F]fluoro, 4-methoxy tyrosine methyl ester N-acetyl) | 14 ± 2% (n = 3) |
| 12c† | (structure with mesityl-I⁺-aryl, ⁻OTs, DOPA methyl ester N-pivaloyl) | (6-[$^{18}$F]fluoro-DOPA methyl ester N-pivaloyl) | 17 ± 6% (n = 3) |

*Radiochemical Yield (RCY) was determined by radio-TLC (average of n runs). The identity of each product was confirmed by HPLC.
†Conditions: Mesityl aryliodonium salt (6 μmol), (CH$_3$CN)$_4$CuOTf (6 μmol), [$^{18}$F]KF•18-crown-6 in DMF (250 μL, 300-700 μCi), total volume 750 μL, 85° C., 20 min.

As demonstrated in Table 7, mesityl aryliodonium salts were converted to the corresponding [$^{18}$F]fluorinated compounds, i.e., acetyl-protected 4-[$^{18}$F]fluoro-$_L$-phenylalanine, acetyl-protected 3-[$^{18}$F]fluorotyrosine, and pivaloyl-protected 6-[$^{18}$F]fluoro-$_L$-DOPA (Examples 12a, 12b, and 12c).

Pivaloyl-protected 6-[$^{18}$F]fluoro-$_L$-DOPA was prepared by the general procedure for automated synthesis of $^{18}$F-labeled compounds described in Example 3 with 1500 mCi initial activity of $^{18}$F. Under automated conditions, the mesityl aryliodonium salt shown in Example 12c was converted to pivaloyl-protected 6-[$^{18}$F]fluoro-$_L$-DOPA in a radiochemical yield (RCY) of 17±2% (ca. 60 mCi) and a (SA) of 4000±2000 Ci/mmol (n=2).

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed is:

1. A method of preparing a radiolabeled aryl fluoride of Formula (2) comprising:

reacting a diaryliodonium salt of Formula (1)

(1)

with an $^{18}$F source in the presence of a copper (I) source selected from CuOTf.toluene and (CH$_3$CN)$_4$CuOTf under conditions sufficient to form the radiolabeled aryl fluoride of Formula (2)

(2)

wherein Ar$^1$ and Ar$^2$ independently are aryl groups; and X$^-$ is an anion.

2. The method of claim 1, wherein Ar$^1$ has a structure of Formula (3):

(3)

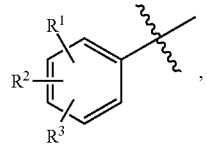

wherein $R^1$, $R^2$, and $R^3$ are independently selected from the group consisting of H, $C_{1-4}$alkyl, $OR^a$, $NR^aR^b$, halo, $-NR^aC(=O)R^b$, $-C(=O)NR^aR^b$, $-OC(=O)R^a$, $-C(=O)OR^a$, $-C(=O)R^a$, aryl, benzyl, and

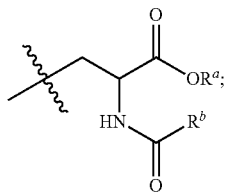

or $R^2$ and $R^3$, taken together with the carbon atoms to which they are attached, form a 4- to 8-membered ring;

$R^a$ is selected from the group consisting of H, $C_{1-4}$alkyl, aryl, and benzyl; and $R^b$ is selected from the group consisting of H, $C_{1-4}$alkyl, aryl, benzyl, $-O-C_{1-4}$alkyl, $-O$-aryl, and $-O$-benzyl;

with the proviso that at least one of $R^1$, $R^2$, and $R^3$ is other than H.

3. The method of claim 2, wherein $R^2$ and $R^3$, taken together with the carbon atoms to which they are attached, form a substituted 4- to 8-membered ring.

4. The method of claim 1, wherein $Ar^1$ is selected from the group consisting of:

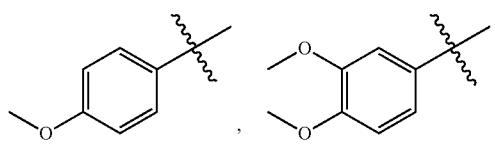

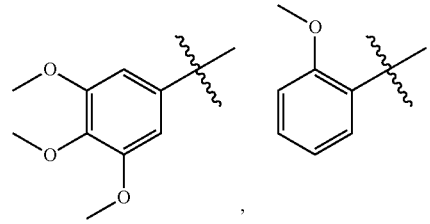

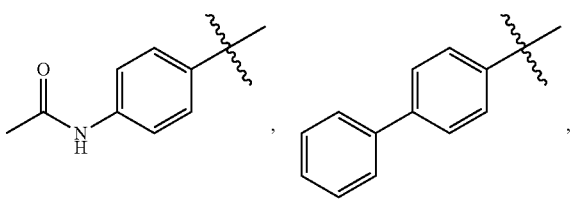

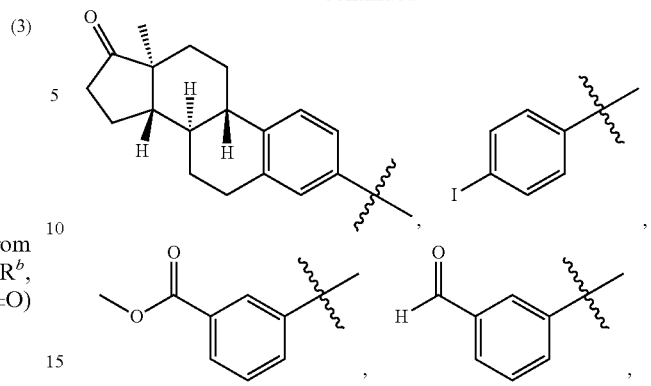

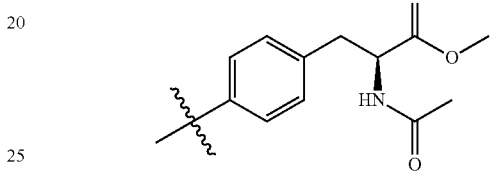

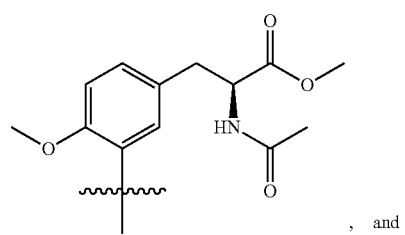

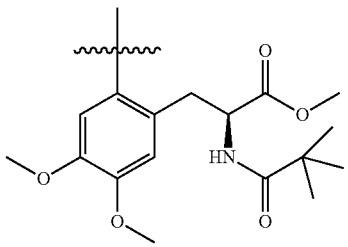

, and

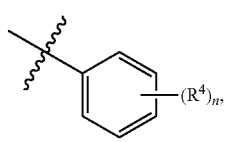

5. The method claim 1, wherein $Ar^2$ has a structure of Formula (4):

(4)

wherein each $R^4$ is independently selected from the group consisting of methyl, ethyl, n-propyl, isopropyl, n-butyl, sec-butyl, iso-butyl, t-butyl, aryl, and benzyl; and n is selected from the group consisting of 1, 2, 3, 4, and 5.

6. The method of claim 5, wherein Ar² is

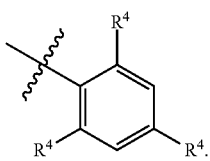

7. The method of claim 1, wherein Ar² is

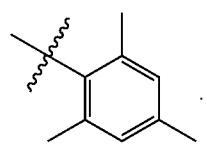 [SMILES: *c1c(C)cc(C)cc1C]

8. The method of claim 1, wherein the diaryliodonium ion is selected from the group consisting of

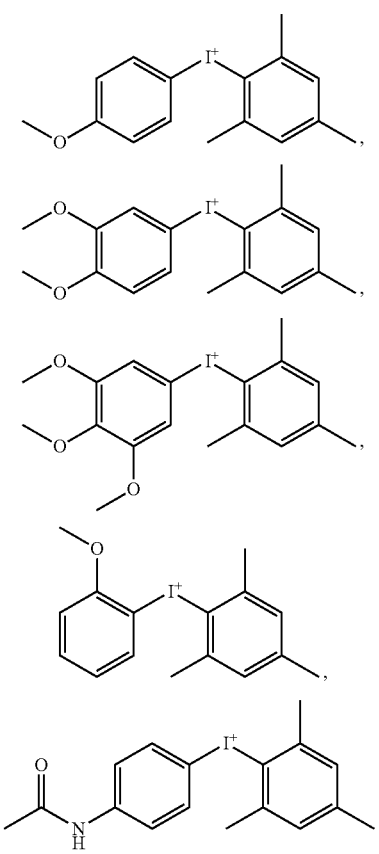

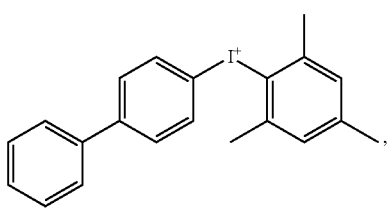

-continued

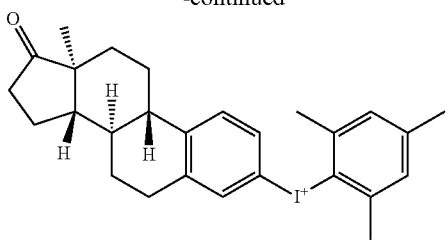

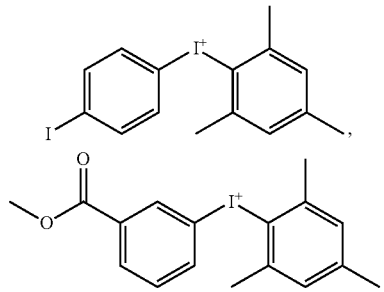

9. The method of claim 1, wherein X⁻ is selected from the group consisting of fluoride, chloride, bromide, iodide, trifluoromethanesulfonate, toluene sulfonate, tetrafluoroborate, hexafluorophosphate, methanesulfonate, hexafluoropropanesulfonate, nonafluorobutanesulfonate, nitrophenyl sulfonate, bromophenyl sulfonate, perfluoroalkyl sulfonate, tetraphenylborate, trifluoroacetate, perfluoroalkylcarboxylate, perchlorate, hexafluorostibate, hexachlorostibate, acetate, and benzoate.

10. The method of claim 1, wherein $X^-$ is $BF_4^-$.

11. The method of claim 1, wherein the $^{18}F$ source is selected from the group consisting of $^{18}F$-labeled alkali metal fluorides, $^{18}F$-labeled alkaline earth metal fluorides, $^{18}F$-labeled ammonium fluorides, and complexes thereof.

12. The method of claim 1, wherein the $^{18}F$ source is selected from the group consisting of $^{18}F$ lithium fluoride, $^{18}F$ sodium fluoride, $^{18}F$ potassium fluoride, $^{18}F$ rubidium fluoride, $^{18}F$ cesium fluoride, $^{18}F$ beryllium fluoride, $^{18}F$ magnesium fluoride, $^{18}F$ calcium fluoride, $^{18}F$-labeled tetraalkylammonium fluorides, and complexes thereof.

13. The method of claim 1, wherein the $^{18}F$ source is selected from the group consisting of $^{18}F$ potassium fluoride and $^{18}F$ potassium fluoride.18-crown-6 complex.

14. The method of claim 1, wherein the $^{18}F$ source comprises a complex with a crown ether, optionally wherein the crown ether is selected from the group consisting of 12-crown-4, 15-crown-5, 18-crown-6, dibenzo-18-crown-6, and diaza-18-crown-6.

15. The method of claim 1, wherein the reacting is carried out at a temperature of about 80° C. to about 90° C.

16. The method claim 1, wherein the reacting is carried out at a molar ratio of the copper (I) source to the diaryliodonium salt of about 1:20 to about 5:1, about 1:10 to about 3:1, about 1:5 to about 2:1, and/or about 1:2 to 1:1.

17. The method of claim 1, wherein the reacting is carried out in a polar aprotic solvent.

18. The method of claim 1, wherein the reacting is carried out in a solvent selected from the group consisting of acetone, methyl ethyl ketone, isophorone, dichloromethane, chloroform, ethyl acetate, dimethylformamide (DMF), dimethyl sulfoxide (DMSO), tetrahydrofuran (THF), acetonitrile, and mixtures thereof.

19. The method of claim 1, further comprising isolating the radiolabeled aryl fluoride of Formula (2).

20. The method of claim 1, wherein the copper (I) source is $(CH_3CN)_4CuOTf$.

21. The method of claim 1, wherein X is $PF_6^-$ or $OTs^-$.

* * * * *